US008545899B2

(12) United States Patent  (10) Patent No.: US 8,545,899 B2
Sharma  (45) Date of Patent: Oct. 1, 2013

(54) TITANIUM DIOXIDE COATINGS HAVING ROUGHENED SURFACES AND METHODS OF FORMING TITANIUM DIOXIDE COATINGS HAVING ROUGHENED SURFACES (75) Inventor: Pramod K. Sharma, Ann Arbor, MI (US)

(73) Assignee: Guardian Industries Corp., Auburn Mills, MI (US)

( * ) Notice: Subject to any disclaimer, the term of this patent is extended or adjusted under 35 U.S.C. 154(b) by 383 days.

(21) Appl. No.: 12/263,968

(22) Filed: Nov. 3, 2008

(65) Prior Publication Data
US 2010/0112024 A1  May 6, 2010

(51) Int. Cl.
A01N 55/10 (2006.01)
B32B 17/00 (2006.01)

(52) U.S. Cl.
USPC .............................. 424/724; 428/701; 428/428

(58) Field of Classification Search
None
See application file for complete search history.

(56) References Cited

U.S. PATENT DOCUMENTS

| | | | |
|---|---|---|---|
| 3,573,470 A | 4/1971 | Haley | |
| 4,504,888 A | 3/1985 | Rosenthal | |
| 5,332,618 A | 7/1994 | Austin | |
| 5,854,169 A | 12/1998 | Heller et al. | |
| 5,950,106 A | 9/1999 | May et al. | |
| 5,981,425 A | 11/1999 | Taoda et al. | |
| 6,013,372 A * | 1/2000 | Hayakawa et al. | 428/411.1 |
| 6,071,606 A | 6/2000 | Yamazaki et al. | |
| 6,103,363 A | 8/2000 | Boire et al. | |
| 6,277,169 B1 | 8/2001 | Hampden-Smith et al. | |
| 6,284,377 B1 | 9/2001 | Veerasamy | |
| 6,344,242 B1 | 2/2002 | Stolk et al. | |
| 6,362,121 B1 | 3/2002 | Chopin et al. | |
| 6,420,437 B1 | 7/2002 | Mori et al. | |
| 7,049,002 B2 | 5/2006 | Greenberg et al. | |
| 7,144,840 B2 | 12/2006 | Yeung et al. | |
| 7,473,369 B2 | 1/2009 | Meng et al. | |
| 7,605,186 B2 | 10/2009 | Chung et al. | |
| 2002/0030188 A1 | 3/2002 | Hayashi et al. | |
| 2002/0150681 A1 | 10/2002 | Boire et al. | |
| 2003/0039843 A1* | 2/2003 | Johnson et al. | 428/432 |
| 2003/0143437 A1 | 7/2003 | Ohtsu et al. | |
| 2003/0235695 A1 | 12/2003 | Greenberg et al. | |
| 2004/0067849 A1 | 4/2004 | Tanaka et al. | |
| 2006/0019028 A1 | 1/2006 | Yeung et al. | |
| 2006/0091079 A1 | 5/2006 | Meng et al. | |
| 2007/0017567 A1 | 1/2007 | Gronet et al. | |
| 2007/0099003 A1 | 5/2007 | Lee et al. | |
| 2007/0146889 A1 | 6/2007 | Wang et al. | |
| 2007/0151482 A1 | 7/2007 | Im et al. | |
| 2008/0020127 A1 | 1/2008 | Whiteford et al. | |
| 2008/0145625 A1 | 6/2008 | Schumacher et al. | |
| 2008/0168919 A1* | 7/2008 | Maehashi | 101/450.1 |
| 2008/0302448 A1 | 12/2008 | Frey et al. | |
| 2009/0061230 A1 | 3/2009 | Berkei et al. | |
| 2009/0214766 A1 | 8/2009 | Magdassi et al. | |
| 2009/0286676 A1 | 11/2009 | Kim et al. | |
| 2011/0045970 A1 | 2/2011 | Sharma et al. | |
| 2011/0076450 A1 | 3/2011 | Sharma et al. | |

FOREIGN PATENT DOCUMENTS

| | | |
|---|---|---|
| EP | 0818561 | 1/1998 |
| EP | 1205243 | 5/2002 |
| EP | 1316532 | 6/2003 |
| JP | 07100378 A | 4/1995 |
| JP | 08-099041 | 4/1996 |
| JP | 08-196903 A | 8/1996 |
| JP | 11-228865 A | 8/1999 |
| JP | 2001-286766 | 10/2001 |
| JP | 2004-092163 A | 3/2004 |
| JP | 2006-198466 A | 8/2006 |
| KR | 10-2004-0024582 A | 3/2004 |
| KR | 10-0421243 B1 | 3/2004 |
| KR | 10-0541750 B1 | 1/2006 |
| KR | 10-0727579 B1 | 6/2007 |
| KR | 10-0753055 B1 | 8/2007 |
| KR | 10-2008-0030981 | 4/2008 |
| WO | WO 97/24471 | 7/1997 |
| WO | WO 03/009061 A2 | 1/2003 |
| WO | 2005105332 | 11/2005 |
| WO | WO 2007/107792 | 9/2007 |
| WO | 2007117332 | 10/2007 |
| WO | WO 2010/028109 A1 | 3/2010 |
| WO | WO 2010/030550 A3 | 3/2010 |
| WO | WO 2010/030551 A1 | 3/2010 |
| WO | WO 2010/030552 | 3/2010 |
| WO | WO 2010/062433 | 6/2010 |
| WO | WO 2011/041218 | 4/2011 |

OTHER PUBLICATIONS

Nissan Chemical, Organosilicasol™, available at http://www.nissanchem-usa.com/organosilicasol.php (May 3, 2013).*
International Search Report in PCT/US2009/0055823 having a mailing date of Feb. 9, 2010.
Written Opinion of the International Searching Authority in PCT/US2009/0055823.
International Search Report in PCT/US2009/0055824 having a mailing date of Apr. 12, 2010.
Written Opinion of the International Searching Authority in PCT/US2009/0055824.
International Search Report in PCT/US2009/0055826 having a mailing date of Feb. 9, 2010.
Written Opinion of the International Searching Authority in PCT/US2009/0055826.
J. Nelson et al., "Photoconductivity and charge trapping in porous nanocrystalline titanium dioxide," *Journal of Photochemistry and Photobiology A: Chemistry*, 148 (2002) 25-31.
T. Watanabe et al., "Photocatalytic activity and photoinduced hydrophilicity of titanium dioxide coated glass," *Thin Solid Films*, 351 (1999) 260-263.
N. Sakai et al., "Effect of Ultrasonic Treatment on Highly Hydrophilic $TiO_2$ Surfaces," *Langmuir*, 1998, 14, 5918-5920.
Y. C. Lee et al, "Photocatalysis and hydrophilicity of doped $TiO_2$ thin films," *Journal of Colloid and Interface Science*, 267, (2003) 127-131.

(Continued)

*Primary Examiner* — Robert A Wax
*Assistant Examiner* — H. Sarah Park
(74) *Attorney, Agent, or Firm* — O'Brien Jones PLLC (57) ABSTRACT

Methods for forming surface roughened titanium dioxide coatings are disclosed. Sol-gel compositions may be prepared having colloidal metal oxide particles and/or colloidal silica particles, formed on a substrate, and subsequently the coated substrate may be heated at a temperature sufficient to form a surface roughened anatase titanium dioxide coating. Surface roughened titanium dioxide coatings having at least one of improved antimicrobial properties, self-cleaning properties, hydrophilicity, and/or activation time are also disclosed. Substrates comprising such coatings are also disclosed.

13 Claims, 4 Drawing Sheets

(56) References Cited

OTHER PUBLICATIONS

S. V. Manorama et al., "Photostabilization of dye on anatase titania nanoparticles by polymer capping," *Journal of Physics and Chemistry of Solids*, 63 (2002) 135-143.

A. Conde-Gallardo et al., "$TiO_2$ anatase thin films deposited by spray pyrolysis of an aerosol of titanium diisopropoxide," *Thin Solid Films*, 473 (2005) 68-73.

K.-H. Haas et al, "Functionalized coatings based on inorganic-organic polymers (ORMOCER®s) and their combination with vapor deposited inorganic thin films," *Surface and Coatings Technology*, 111 (1999) 72-79.

R. van Grieken et al., Synthesis of size-controlled silica-supported $TiO_2$ photocatalysts, *Journal of Photochemistry and Photobiology A: Chemistry*, 148 (2002) 315-322,.

Co-pending U.S. Appl. No. 12/207,359, filed Sep. 9, 2008.
Co-pending U.S. Appl. No. 12/207,235, filed Sep. 9, 2008.
Co-pending U.S. Appl. No. 12/207,167, filed Sep. 9, 2008.
Co-pending U.S. Appl. No. 12/207,076, filed Sep. 9, 2008.
Co-pending U.S. Appl. No. 12/263,991, filed Nov. 3, 2008.
Office Action dated Apr. 9, 2009 from U.S. Appl. No. 12/207,235.
Office Action dated Apr. 15, 2009 from U.S. Appl. No. 12/207,359.
Office Action dated Sep. 30, 2009 from U.S. Appl. No. 12/207,359.
Office Action dated Nov. 12, 2009 from U.S. Appl. No. 12/207,235.
Office Action dated Apr. 12, 2010 from U.S. Appl. No. 12/207,235.
Aubry, E. et al., "Poisoning prevention of TiO2 photocatalyst coatings sputtered on soda-lime glass by intercalation of SiNx diffusion barriers" Surface & Coatings Technology 201, 2007, pp. 7706-7712.
He, C. et al., "Influence of silver doping on the photocatalytic activity of titania films" Applied Surface Science 200, 2002, pp. 239-247.
Page, K et al., "Titania and silver-titania composite films on glass—potent antimicrobial coatings" Journals of Materials Chemistry 17, 2007, pp. 95-104.
Seery, M. et al., "Silver doped titanium dioxide nanomaterials for enhanced visible light photocatalysis" Journal of Photochemistry and Photobiology 189, 2007, pp. 258-263.
European Search Report for European Application No. EP 09813467.9 dated Oct. 21, 2011.
International Search Report and Written Opinion for International Publication No. WO 2010/030552 (International Application No. PCT/US2009/055827) dated Apr. 20, 2010.
International Search Report and Written Opinion for International Publication No. WO 2010/062433 (International Application No. PCT/US2009/055829) dated Mar. 10, 2010.
International Search Report and Written Opinion for International Publication No. WO 2011/041218 (International Application No. PCT/US2010/050118) dated Jun. 23, 2011.
U.S. Notice of Allowance dated Apr. 12, 2010 from co-pending U.S. Appl. No. 12/207,359.
U.S. Notice of Allowance dated Jul. 29, 2010 from co-pending U.S. Appl. No. 12/207,359.
U.S. Office Action dated Dec. 3, 2010 from co-pending U.S. Appl. No. 12/207,235.
U.S. Office Action dated Jun. 16, 2011 from co-pending U.S. Appl. No. 12/207,235.
U.S. Office Action dated Oct. 5, 2011 from co-pending U.S. Appl. No. 12/207,235.
U.S. Office Action dated Jun. 17, 2011 from co-pending U.S. Appl. No. 12/207,167.
U.S. Office Action dated Nov. 21, 2011 from co-pending U.S. Appl. No. 12/207,167.
U.S. Office Action dated Apr. 7, 2011 from co-pending U.S. Appl. No. 12/207,076.
U.S. Office Action dated Oct. 7, 2011 from co-pending U.S. Appl. No. 12/207,076.
U.S. Office Action dated Apr. 20, 2011 from co-pending U.S. Appl. No. 12/263,991.
U.S. Office Action dated Oct. 11, 2011 from co-pending U.S. Appl. No. 12/263,991.
Imai et al., "Preparation of Porous Anatase Coating from Sol-Gel-Derived Titanium Dioxide and Titanium Dioxide-Silica by Water-Vapor Exposure," Journal of American Ceramic Society, 82 [9], Jan. 1, 1999, (pp. 2301-2304).
Jung et al., "Photoactivity of SiO2/TiO2 and ZrO2/TiO2 Mixed Oxides Prepared by Sol-Gel Method," Material Letters 58 (2004), (pp. 2897-2900).
Advisory Action dated Nov. 30, 2012 issued in co-pending U.S. Appl. No. 12/569,177.
Advisory Action dated Jun. 27, 2012 issued in co-pending U.S. Appl. No. 12/207,076.
U.S. Notice of Allowance dated Oct. 17, 2012 issued in co-pending U.S. Appl. No. 12/207,076.
U.S. Office Action dated Apr. 18, 2012 issued in co-pending U.S. Appl. No. 12/207,235.
U.S. Office Action dated Aug. 22, 2012 issued in co-pending U.S. Appl. No. 12/207,235.
U.S. Office Action dated Jul. 16, 2012 issued in co-pending U.S. Appl. No. 12/569,177.
U.S. Office Action dated Mar. 14, 2012 issued in co-pending U.S. Appl. No. 12/569,177.
European Search Report for EP 09813466 dated Feb. 6, 2012.
U.S. Office Action dated Jan. 17, 2013 issued in co-pending U.S. Appl. No. 12/914,102.
U.S. Office Action dated Feb. 4, 2013 issued in co-pending U.S. Appl. No. 12/263,991.

\* cited by examiner

TITANIUM DIOXIDE COATINGS HAVING ROUGHENED SURFACES AND METHODS OF FORMING TITANIUM DIOXIDE COATINGS HAVING ROUGHENED SURFACES

FIELD

The present invention relates generally to titanium dioxide coatings having roughened surfaces and methods of forming titanium dioxide coatings having roughened surfaces.

BACKGROUND

Titanium dioxide ($TiO_2$, also know as titania) has been widely studied because of its potential photocatalytic applications. Titanium dioxide only absorbs ultraviolet (UV) radiation. When UV light is illuminated on titanium dioxide, electron-hole pairs are generated. Electrons are generated in the conduction band and holes are generated in the valence band. The electron and hole pairs reduce and oxidize, respectively, adsorbates on the surface of the titanium dioxide, producing radical species such as $OH^-$ and $O_2^-$. Such radicals may decompose certain organic compounds. As a result, titanium dioxide coatings have found use in antimicrobial and self-cleaning coatings, for example on windows.

To activate the titanium dioxide to photogenerate these electron-hole pairs (i.e. photocatalytic activity), and thus to provide the titanium dioxide with antimicrobial and/or self-cleaning properties, titanium dioxide must be regularly dosed with photons of energy greater than or equal to about 3.0 eV (i.e., radiation having a wavelength less than about 413 nm). Depending on variables such as the structure, ingredients, and texture of titanium dioxide coatings, for example, dosing may takes several hours, such as, for example, 6 hours or more. Antimicrobial titanium dioxide coatings, therefore, must generally be exposed to UV radiation for at least 6 hours before achieving the full photocatalytic effect.

Efforts have been made to extend the energy absorption of titanium dioxide to visible light and to improve the photocatalytic activity of titanium dioxide. For example, foreign metallic elements such as silver can be added. This may, for example, aid electron-hole separation as the silver can serve as an electron trap, and can facilitate electron excitation by creating a local electric field. The use of silver, however, requires tempering the coating in a nitrogen environment to prevent the silver from oxidizing. Thus, adding silver to titanium dioxide coatings on a large scale is not a viable option due to the high costs.

Titanium dioxide also has been shown to exhibit highly hydrophilic properties when exposed to UV radiation. Such hydrophilicity may be beneficial in certain embodiments, such as, for example, certain coating embodiments. Without wishing to be limited in theory, it is believed that the photo-induced hydrophilicity is a result of photocatalytic splitting of water by the mechanism of the photocatalytic activity of the titanium dioxide, i.e., by the photogenerated electron-hole pairs. When exposed to UV radiation, the water contact angle of titanium dioxide coatings approaches 0°, i.e., superhydrophilicity.

Current coating methods involving titanium dioxide often result in a disadvantageous loss of hydrophilicity and/or photocatalytic activity such as antimicrobial and/or self-cleaning properties of the titanium dioxide. This may be due to formation of different phases of the titanium dioxide during the coating process. For example, anatase titanium dioxide typically transforms to rutile phase titanium dioxide when heated at temperatures which may be used during the coating process, such as temperatures greater than 600° C., such as may be used during the coating process. The rutile phase has less desirable surface coating properties than the anatase phase, such as, for example, less desirable hydrophilicity and antimicrobial and/or self-cleaning properties.

There is thus a long-felt need in the industry for methods for forming a titanium dioxide coating having increased photocatalytic activity such as antimicrobial and/or self-cleaning properties and/or hydrophilicity, and/or a reduced dosing time. The invention described herein may, in some embodiments, solve some or all of these needs.

SUMMARY

In accordance with various exemplary embodiments of the invention, methods for improving at least one of the hydrophilicity, activation time, and/or photocatalytic activity (and thus antimicrobial and/or self-cleaning properties) of titanium dioxide coatings have now been discovered.

Various exemplary embodiments of the invention relate to methods for forming anatase titanium dioxide coatings having roughened surfaces. At least one exemplary embodiment of the invention relates to methods for forming anatase titanium dioxide coatings comprising preparing a sol-gel composition comprising colloidal metal oxide and/or colloidal silica, coating a substrate with the sol-gel composition, and then heating the coating to form an anatase titanium dioxide coating having a roughened surface.

Other exemplary embodiments of the invention relate to surface roughened anatase titanium dioxide coatings having at least one improved property chosen from antimicrobial and/or self-cleaning properties, hydrophilicity, and/or activation time. Exemplary embodiments of the invention also include antimicrobial and/or self-cleaning coatings comprising surface roughened anatase titanium coatings. Further embodiments include a substrate coated with a titanium dioxide coating according to various exemplary embodiments of the invention.

As used herein, "increased" or "improved photocatalytic activity" means any decrease in the activation time of, or any increase in the amount of organic material decomposed by, the titanium dioxide coating in a specified period of time when compared to coatings not according to various embodiments of the invention. Similarly, "increased" or "improved antimicrobial properties" or "increased" or "improved self-cleaning properties" likewise mean any increase in the amount of organic material decomposed by the titanium dioxide coating in a specified period of time when compared to coatings not according to various embodiments of the invention.

Throughout this disclosure, the terms "photocatalytic activity," "antimicrobial properties," and/or "self-cleaning properties" may be used interchangeably to convey that the antimicrobial and/or self-cleaning properties of the titanium dioxide coatings are a result of the photocatalytic activity of the coatings.

As used herein, "activation time" means the time required for a titanium dioxide coating illuminated with UV radiation to decompose a specified percentage of organic material over a period of time. Likewise, "decreased" or "reduced activation time" means any decrease in the amount of activation time required to decompose the specified percentage of organic material over a period of time when compared to coatings not according to various embodiments of the invention.

As used herein, "increased" or "improved hydrophilicity" means any decrease in the water contact angle when compared to coatings not according to various embodiments of the invention. The water contact angle is a measure of the angle between water and the surface of a material. A smaller water contact angle indicates a material that is more hydrophilic than a material with a higher water contact angle. Water droplets on more hydrophilic surfaces tend to spread out or flatten, whereas on less hydrophilic surfaces water tends to bead up or form droplets which are more spherical in shape, and the water contact angle of those surfaces is generally greater.

As used herein, the term "sol-gel composition" means a chemical solution comprising a titanium compound within the chemical solution that forms a polymerized titanium dioxide coating when the solvent is removed, such as by heating or any other means.

As used herein, the term "temperable" means a titanium dioxide coating that may be heated to a temperature sufficient to temper a substrate on which it is formed without forming rutile phase titanium dioxide.

As used herein, the term "laminate" means an object having a layered structure. For example, a laminate may comprise a substrate, such as glass, and a coating, such as a sol-gel coating comprising colloidal metal oxide particles or colloidal silica particles, formed thereon. A laminate according to the present invention may be made by any process known in the art to produce layers or coatings.

As described herein, the invention relates to surface roughened anatase titanium dioxide coatings and methods of forming surface roughened anatase titanium dioxide coatings. In the following description, certain aspects and embodiments will become evident. It should be understood that the invention, in its broadest sense, could be practiced without having one or more features of these aspects and embodiments. It should be understood that these aspects and embodiments are merely exemplary and explanatory, and are not restrictive of the invention as claimed.

BRIEF DESCRIPTION OF THE DRAWINGS

The following figures, which are described below and which are incorporated in and constitute a part of the specification, illustrate exemplary embodiments of the invention and are not to be considered limiting of the scope of the invention, for the invention may admit to other equally effective embodiments.

DESCRIPTION OF EXEMPLARY EMBODIMENTS

Reference will now be made to various exemplary embodiments of the invention, examples of which are illustrated in the accompanying figures. However, these various exemplary embodiments are not intended to limit the disclosure, but rather numerous specific details are set forth in order to provide a thorough understanding of the invention. It will be apparent to one skilled in the art that the invention may be practiced without some or all of these specific details, and the disclosure is intended to cover alternatives, modifications, and equivalents. For example, well-known features and/or process steps may not have been described in detail so as not to unnecessarily obscure the invention.

The present invention contemplates various exemplary methods of forming anatase titanium dioxide coatings having a roughened surface in order to improve at least one of photocatalytic activity (and thus antimicrobial and/or self-cleaning properties), hydrophilicity, and/or activation time of the coating.

While not wishing to be bound by theory, it is believed that the roughened surface increases the number of attainable surface activation sites. An increase in the number of attainable surface activation sites may lead to (1) improved photocatalytic activity such as antimicrobial and/or self-cleaning properties because the number of radicals may be directly related to the amount of surface area available, and/or (2) improved hydrophilicity because the number of radicals which are present and are available to be attracted to the water molecules is greater.

At least one exemplary embodiment of the invention contemplates methods of forming, on a substrate, anatase titanium dioxide coatings having roughened surfaces comprising preparing a titanium dioxide sol-gel composition comprising colloidal metal oxide particles or colloidal silica particles, coating the substrate with the sol-gel composition, and heating the coating to form a surface roughened anatase titanium dioxide coating.

Colloidal metal oxide particles that may be used according to at least one embodiment of the present invention may include particles of any metal oxide that is transparent or nearly transparent and does not interact with titanium dioxide to form phases other than the anatase phase. By way of example, metal oxides that are amorphous at temperatures up to about 700° C. may be used according to various embodiments of the invention. In the exemplary embodiments below, the sol gel composition comprises colloidal silica. However, one of ordinary skill in the art will appreciate that other metal oxides may be used as described above.

In at least one exemplary embodiment, the titanium dioxide sol-gel composition comprises a titanium alkoxide or a titanium chloride. Examples of titanium alkoxides which may be used in sol-gel compositions according to the present invention include, but are not limited to, titanium n-butoxide, titanium tetra-iso-butoxide (TTIB), titanium isopropoxide, and titanium ethoxide. In at least one embodiment, the titanium dioxide sol-gel composition comprises titanium tetra-iso-butoxide.

In at least one embodiment, the sol-gel composition further comprises a surfactant, which may improve the coating process. Examples of surfactants which may be used in accordance with the present invention include, but are not limited to, non-ionic surfactants such as alkyl polysaccharides, alkylamine ethoxylates, castor oil ethoxylates, ceto-stearyl alcohol ethoxylates, decyl alcohol ethoxylates, and ethylene glycol esters.

In various exemplary embodiments, the sol gel composition may comprise colloidal metal oxide particles or colloidal silica particles having an average particle size as large as about 200 nm. According to at least one exemplary embodiment, the colloidal silica comprises silica particles having an average particle size less than 100 nm. In another exemplary embodiment, the silica particles have an average particle size of about 70 nm. One skilled in the art would appreciate that the choice of particle size depends on, for example, the particular particles chosen and the desired surface properties of the titanium dioxide coating. For example, smaller silica particle sizes may result in a lower surface roughness given a predetermined concentration of colloidal silica in the sol gel composition, while larger silica particle sizes may result in greater surface roughness at the same predetermined concentration of colloidal silica in the sol gel composition. Similarly, the choice of silica particle size may also be based on the desired thickness of the titanium dioxide coating. For a thinner titanium dioxide coating, it may be desirable to use smaller silica particles, whereas larger silica particles may be used for thicker titanium dioxide coatings. In at least one embodiment, the silica particles have a narrow size distribution.

In at least one exemplary embodiment of the invention, the sol gel composition comprises colloidal metal oxide or colloidal silica in an amount less than or equal to about 20 wt % relative to the total weight of the composition. In other embodiments, the sol gel composition comprises colloidal metal oxide or colloidal silica in an amount less than or equal to about 15 wt %, less than or equal to 10 wt %, less than or equal to 5 wt %, or less than or equal to 2 wt % relative to the total weight of the coating. In various embodiments, the sol gel composition comprises colloidal metal oxide or colloidal silica in an amount ranging from about 5 wt % to about 15 wt % relative to the total weight of the composition.

In other exemplary embodiments, a colloidal metal oxide or silica concentration greater than about 15 wt % can be used. One skilled in the art will appreciate that additional colloidal metal oxide or silica may result in increased surface roughness, but other effects may negatively impact the performance of the surface roughened titanium dioxide coating. For example, additional silica in the titanium dioxide coating may decrease the photocatalytic activity of the coating. Accordingly, the amount of colloidal metal oxide or colloidal silica which can be used in any specific embodiment of the invention may easily be determined by one of skill in the art, in view of the desired properties of the coating.

In at least one embodiment, the surface roughened titanium dioxide coating may have a thickness ranging from, for example, about 50 nm to about 500 nm. In at least one embodiment, the surface roughened titanium dioxide coating has a thickness ranging from about 100 nm to about 350 nm, or from about 150 nm to about 300 nm. One skilled in the art will appreciate that the thickness of the titanium dioxide coating may be chosen based on the desired properties of the coating, such as, for example, scratch resistance, durability, light transmission, etc.

Embodiments of surface roughened titanium dioxide coatings may exhibit a mean square roughness, as measured using an atomic force microscope (AFM) technique, ranging from about 2 nm to about 20 nm. Surface roughening greater than about 20 nm can also be achieved by using larger metal oxide or silica particles in the sol gel composition. In at least one embodiment, the titanium dioxide coating may have a mean square roughness ranging from, for example, about 5 nm to about 15 nm, or from about 8 nm to about 12 nm.

In various exemplary embodiments, the surface roughened anatase titanium dioxide coatings may be formed on a substrate. Accordingly, substrates coated with a surface roughened titanium dioxide coating according to various exemplary embodiments of the invention are also contemplated herein. One of skill in the art will readily appreciate the types of substrates which may be coated with exemplary coatings as described herein.

In one exemplary embodiment, the substrate may comprise a glass substrate. By way of example only, the glass substrate may be chosen from standard clear glass, such as float glass, matte/matte, and matte/prismatic, or a low iron glass, such as ExtraClear™, UltraWhite™, or Solar glasses available from Guardian Industries.

In at least one embodiment, the substrate may be coated with the sol-gel composition by a method chosen from spin-coating the sol-gel composition on the substrate, spray-coating the sol-gel composition on the substrate, dip-coating the substrate with the sol-gel composition, and any other technique known to those of skill in the art.

In one exemplary embodiment, the sol-gel coated substrate may be heated at a temperature of 600° C. or greater, such as 625° C. or greater. In one exemplary embodiment, the sol-gel coated substrate may be heated for any length time sufficient to create a surface roughened anatase titanium dioxide coating, such as, for example, about 3-4 minutes, such as, about 3½ minutes. One skilled in the art will appreciate, however, that other temperatures and heating times may be used and should be chosen such that anatase titanium dioxide coating is formed. For example, the titanium dioxide coatings according to exemplary embodiments of the invention as described herein may be heated at a temperature ranging from about 550° C. to about 650° C. The titanium dioxide coatings may be heated at lower temperatures as well, as long as anatase titanium dioxide is formed. Thus, one skilled in the art may choose the temperature and heating time based on, for example, the appropriate temperature and time for heating to form the surface roughened anatase titanium dioxide coating, the properties of the desired surface roughened titanium dioxide coating, such as thickness of the coating or thickness of the substrate, etc. For example, a thinner coating may require heating at a lower temperature or for a shorter time than a thicker coating. Similarly, a substrate that is thicker or has lower heat transfer may require a higher temperature or a longer time than a substrate that is thinner or has a high heat transfer. As used herein, the phrase "heated at" a certain temperature means that the oven or furnace is set at the specified temperature. Determination of the appropriate heating time and temperature is well within the ability of those skilled in the art, requiring no more than routine experimentation.

Temperable anatase titanium dioxide coatings may be formed according to at least one method of the present invention. For example, an anatase titanium dioxide coating formed on a glass substrate may be heated at a temperature sufficient to temper the glass substrate without forming the rutile phase of titanium dioxide, i.e., the titanium dioxide remains in the anatase phase when the glass substrate is tempered.

The present invention also contemplates, in at least one embodiment, a surface roughened anatase titanium dioxide coating. Such coatings may, in certain embodiments, have properties chosen from increased photocatalytic activity (and thus antimicrobial and/or self-cleaning properties), hydrophilicity, and/or decreased activation time.

Various exemplary methods in accordance with the invention may improve at least one of hydrophilicity and photocatalytic activity such as antimicrobial and/or self-cleaning properties of the coatings.

In at least one embodiment, the surface roughened titanium dioxide coating may be used as an antimicrobial and/or self-cleaning coating. Accordingly, a substrate having improved antimicrobial and/or self-cleaning properties, coated with a surface roughened titanium dioxide coating according to various embodiments of the invention, can be provided. Antimicrobial and/or self-cleaning coatings according to the present invention may be used, for example, on windows.

The present invention also contemplates an antimicrobial and/or self-cleaning laminate. According to at least one embodiment, the antimicrobial and/or self-cleaning laminate may comprise a substrate and a surface roughened titanium dioxide coating on the substrate.

The present invention also contemplates, in at least one embodiment, a surface roughened titanium dioxide coating having improved hydrophilicity, such as, for example, when formed on a substrate.

The present invention is further illustrated by the following non-limiting examples, which are provided to further aid those of skill in the art in the appreciation of the invention.

Unless otherwise indicated, all numbers herein, such as those expressing weight percents of ingredients and values for certain physical properties, used in the specification and claims are to be understood as being modified in all instances by the term "about," whether so stated or not. It should also be understood that the precise numerical values used in the specification and claims form additional embodiments of the invention. Efforts have been made to ensure the accuracy of the numerical values disclosed in the Examples. Any measured numerical value, however, can inherently contain certain errors resulting from the standard deviation found in its respective measuring technique.

As used herein, a "wt %" or "weight percent" or "percent by weight" of a component, unless specifically stated to the contrary, is based on the total weight of the composition or article in which the component is included. As used herein, all percentages are by weight unless indicated otherwise.

It is noted that, as used in this specification and the appended claims, the singular forms "a," "an," and "the," include plural referents unless expressly and unequivocally limited to one referent, and vice versa. Thus, by way of example only, reference to "a substrate" can refer to one or more substrates, and reference to "a surface roughened titanium dioxide coating" can refer to one or more surface roughened titanium dioxide coatings. As used herein, the term "include" and its grammatical variants are intended to be non-limiting, such that recitation of items in a list is not to the exclusion of other like items that can be substituted or added to the listed items.

It will be apparent to those skilled in the art that various modifications and variation can be made to the present disclosure without departing from the scope its teachings. Other embodiments of the disclosure will be apparent to those skilled in the art from consideration of the specification and practice of the teachings disclosed herein. It is intended that the embodiments described in the specification be considered as exemplary only.

EXAMPLES

Comparative Example

Figure 1:
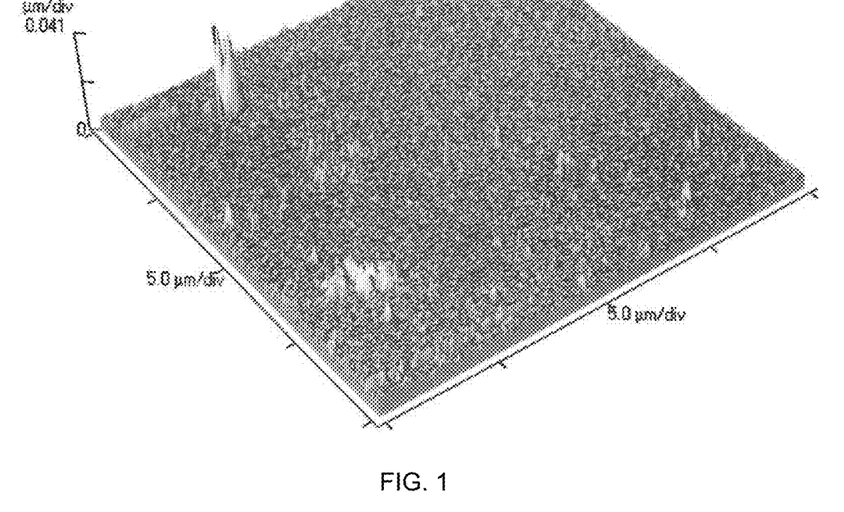
FIG. 1 is an AFM micrograph of the titanium dioxide coating of the Comparative Example.

A titanium dioxide sol was prepared by mixing 6 grams of titanium tetra-iso-butoxide (TTIB) in a solution containing 25 g of ethanol and 2 grams of nitric acid. The mixture was stirred for 1 hour. The pure titanium dioxide coating was fabricated by spin coating a glass substrate at 700 rpm for 30 seconds. The coating was heat treated in a furnace at 625° C. for 3½ minutes. The formed titanium dioxide coating was pure anatase phase titanium dioxide. The anatase titanium dioxide coating had a thickness of 103.6 nm, a water contact angle of 19.1°, and a mean square roughness of 2.11 nm. The titanium dioxide coating had a visible light transmission of 77.7%, reflection at the film side of 17.31%, and 0.48% haze. The color components of the titanium dioxide coating were 2.46 and 20.46 for the a* component and the b* component, respectively. An AFM micrograph of the titanium dioxide coating of the Comparative Example is shown in FIG. 1.

The photocatalytic activity of the examples disclosed herein was tested using a stearic acid test that measured the degradation of stearic acid on the anatase titanium dioxide coatings. To perform the stearic acid test, an $8.8 \times 10^{-3}$ M stearic acid/methanol solution was prepared. The stearic acid/methanol solution was spin coated on the surface of the anatase titanium dioxide coating at 2000 rpm for 30 seconds. The stearic acid concentration was measured with a Nicolet 6700 FT-IR spectrometer by integrating the absorption peaks of the stearic acid molecule between 2700 and 3100 $cm^{-1}$. Stearic acid concentration was then measured at various time intervals of UV illumination of the anatase titanium dioxide coating. Two UV lamps with 1300 $\mu W/cm^2$ and wavelength of 340 nm were used for UV irradiation.

The titanium dioxide coating of the Comparative Example had 61.39% of the stearic acid after exposing the coating to UV radiation for 120 minutes. After 240 minutes of UV exposure, 39.19% of the stearic acid was left on the titanium dioxide coating of the comparative example. 12.65% of the stearic acid remained after 360 minutes of UV exposure.

Example 1

The titanium dioxide sol used to prepare the titanium dioxide coating of Example 1 was prepared similar to the titanium dioxide sol of the Comparative Example. To the titanium dioxide sol was added 2 wt % of colloidal silica having a particle size of 70 nm (IPA-ST-Z1 from Nissan Chemical). The colloidal silica particles led to a rough surface of the titanium dioxide coating after spin-coating and heating was performed as above in the Comparative Example.

The water contact angle of the surface roughened anatase titanium dioxide coating of Example 1 was 17.12°, and the coating had a mean square roughness of 10.84 nm. The thickness of the coating was 171.2 nm. The visible light transmission, reflectance at the film side, and haze of the coating of Example 1 were 83.8%, 13.12%, and 0.72%, respectively. Color components a* and b* of the coating were 5.31 and 2, respectively.

After 120 minutes of UV exposure during the stearic acid test, the titanium dioxide coating of Example 1 had 10.34% of the stearic acid remaining. After 240 minutes and after 360 minutes, the stearic acid concentration was 9.23% and 3.58%, respectively.

Example 2

The titanium dioxide sol used to prepare the titanium dioxide coating of Example 2 was prepared similar to the titanium dioxide sol of the Comparative Example. To the titanium dioxide sol was added 5 wt % of colloidal silica having a particle size of 70 nm (IPA-ST-Z1 from Nissan Chemical). The colloidal silica particles led to a rough surface of the titanium dioxide coating after spin-coating and heating was performed as above in the Comparative Example.

The water contact angle of the silver oxide surface roughened anatase titanium dioxide coating of Example 2 was 16.01°, and the coating had a mean square roughness of 10.38 nm. The thickness of the coating was 220.2 nm. The visible light transmission, reflectance at the film side, and haze of the coating of Example 2 were 87.00%, 11.38%, and 0.71%, respectively. Color components a* and b* of the coating were 2.16 and −8.42, respectively.

After 120 minutes of UV exposure during the stearic acid test, the titanium dioxide coating of Example 2 had 12.86% of the stearic acid remaining. After 240 minutes and after 360 minutes, the stearic acid concentration was 2.10% and 1.98%, respectively.

Example 3

The titanium dioxide sol used to prepare the titanium dioxide coating of Example 3 was prepared similar to the titanium dioxide sol of the Comparative Example. To the titanium dioxide sol was added 10 wt % of colloidal silica having a particle size of 70 nm (IPA-ST-Z1 from Nissan Chemical). The colloidal silica particles led to a rough surface of the titanium dioxide coating after spin-coating and heating was performed as above in the Comparative Example.

The water contact angle of the silver oxide surface roughened anatase titanium dioxide coating of Example 3 was 16.12°, and the coating had a mean square roughness of 11.21 nm. The thickness of the coating was 301.4 nm. The visible light transmission, reflectance at the film side, and haze of the coating of Example 3 were 88.00%, 10.21%, and 0.86%, respectively. Color components a* and b* of the coating were 0.66 and −3.79, respectively.

After 120 minutes of UV exposure during the stearic acid test, the titanium dioxide coating of Example 3 had 3.14% of the stearic acid remaining. After 240 minutes and after 360 minutes, the stearic acid concentration was 1.22% and 1.50%, respectively.

Example 4

Figure 2:
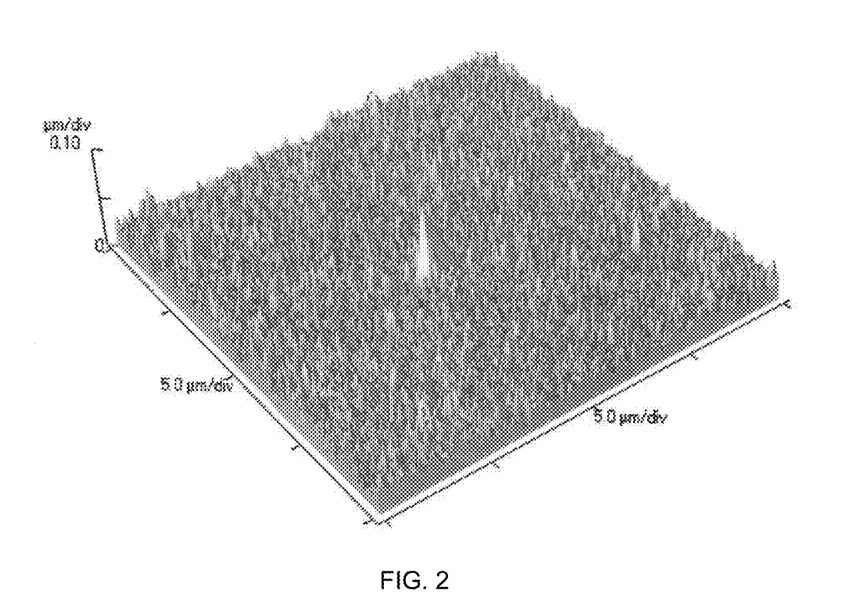
FIG. 2 is an AFM micrograph of the surface roughened anatase titanium dioxide coating of Example 4.

The titanium dioxide sol used to prepare the titanium dioxide coating of Example 4 was prepared similar to the titanium dioxide sol of the Comparative Example. To the titanium dioxide sol was added 15 wt % of colloidal silica having a particle size of 70 nm (IPA-ST-Z1 from Nissan Chemical). The colloidal silica particles led to a rough surface of the titanium dioxide coating after spin-coating and heating was performed as above in the Comparative Example. An AFM micrograph of the surface roughened titanium dioxide coating of Example 4 is shown in FIG. 2.

The water contact angle of the silver oxide surface roughened anatase titanium dioxide coating of Example 4 was 14.89°, and the coating had a mean square roughness of 11.76 nm. The thickness of the coating was 262.5 nm. The visible light transmission, reflectance at the film side, and haze of the coating of Example 4 were 88.90%, 8.71%, and 1.00%, respectively. Color components a* and b* of the coating were 1.92 and −5.48, respectively.

After 120 minutes of UV exposure during the stearic acid test, the titanium dioxide coating of Example 4 had 6.03% of the stearic acid remaining. After 240 minutes and after 360 minutes, the stearic acid concentration was 2.53% and 3.32%, respectively.

Figure 3:
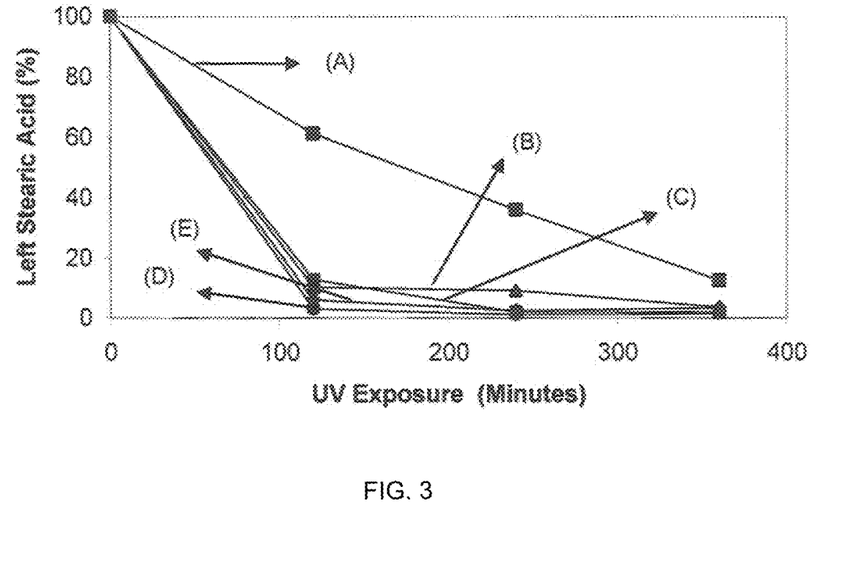
FIG. 3 is a graph of a stearic acid test showing the amount of stearic acid remaining after UV exposure for the titanium dioxide coatings of the Examples.
Figure 4:
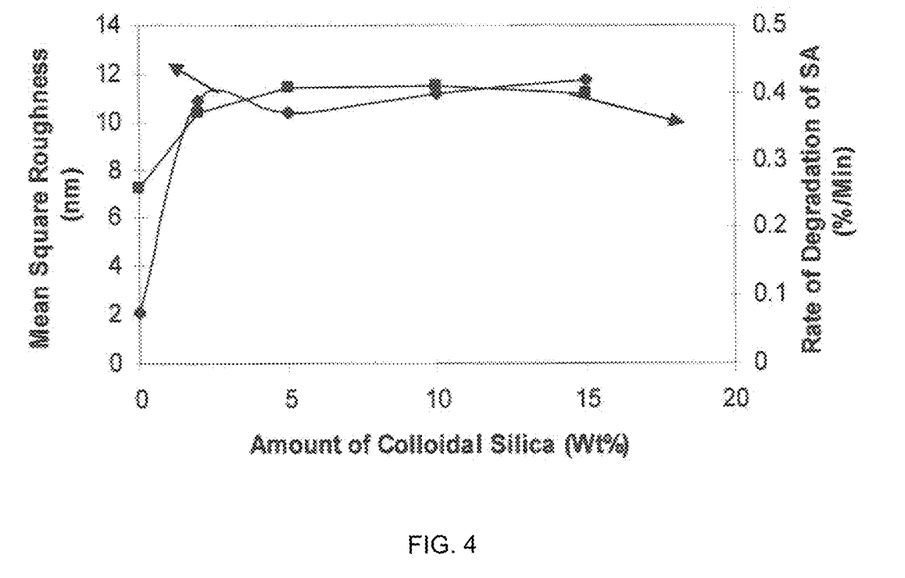
FIG. 4 is a graph of the mean square roughness and rate of degradation of stearic acid plotted against the amount of colloidal silica in the titanium dioxide coatings of the Examples.

As demonstrated by Examples 1-4, surface roughened anatase titanium dioxide coatings increase the photocatalytic activity (antimicrobial and/or self-cleaning properties) of anatase titanium dioxide. The amount of stearic acid left on the titanium dioxide coatings of the Comparative Example (A), Example 1(B), Example 2(C), Example 3(D), and Example 4(E), is shown in FIG. 3. The rate of degradation as a function of the amount of colloidal silica in the titanium dioxide coatings is shown in FIG. 4.

Figure 5:
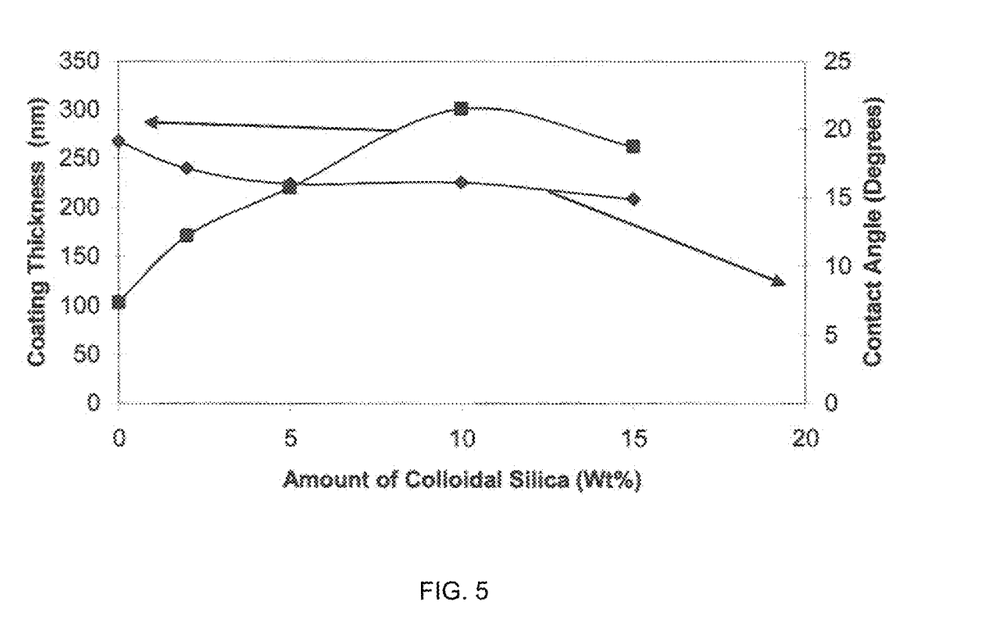
FIG. 5 is a graph of the coating thickness and contact angle as a function of the amount of colloidal silica in the titanium dioxide coatings of the Examples.

In addition, the surface roughened anatase titanium dioxide coatings had lower water contact angles than the titanium dioxide coating of the Comparative Example, as seen in the graph of FIG. 5.

Figure 6:
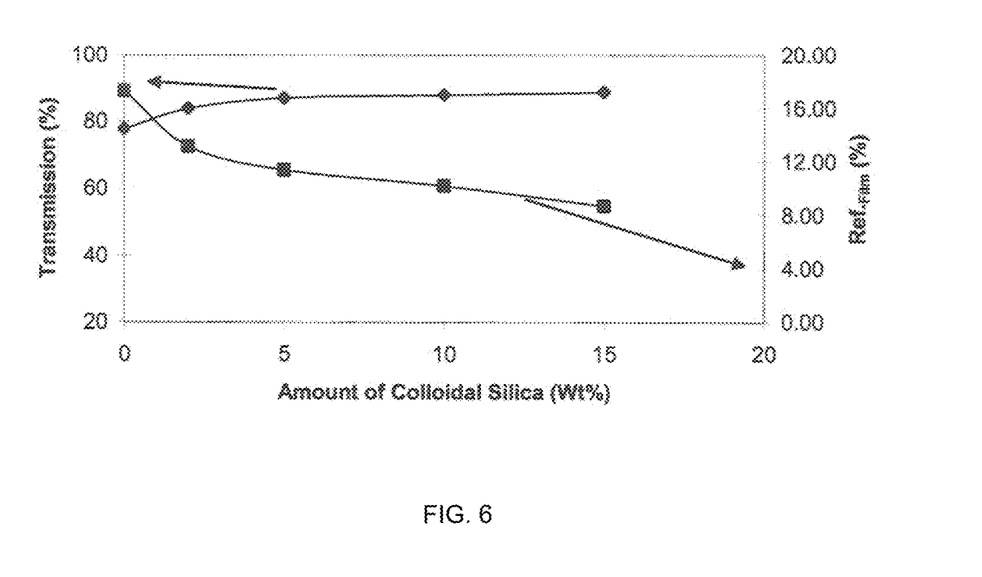
FIG. 6 is a graph of the transmission and reflection of at the film side as a function of the amount of colloidal silica in the titanium dioxide coatings of the Examples.
Figure 7:
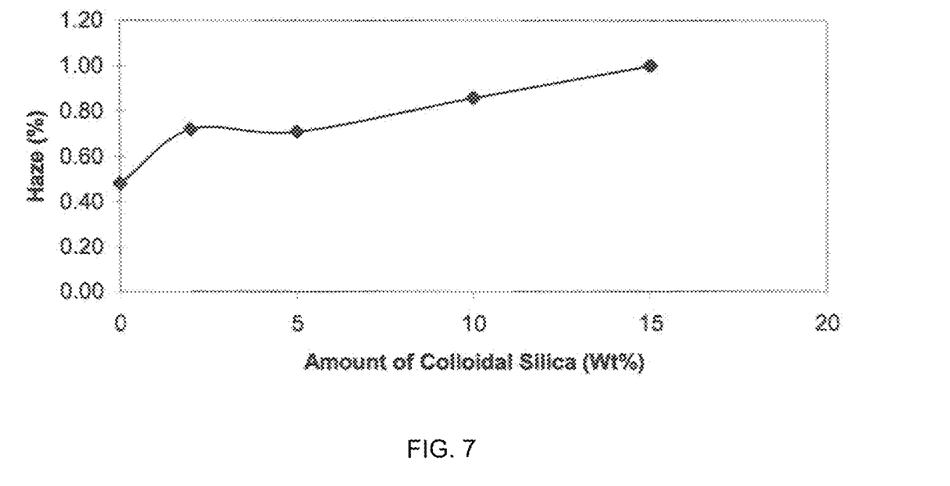
FIG. 7 is a graph of the haze as a function of the amount of colloidal silica in the titanium dioxide coatings of the Examples.

Graphs of the transmission of visible light, reflection at the film side, and haze are shown in FIGS. 6 and 7. As seen in FIG. 6, an increase in the amount of colloidal silica resulted in a decrease in reflected light and an increase in light transmission.

Figure 8:
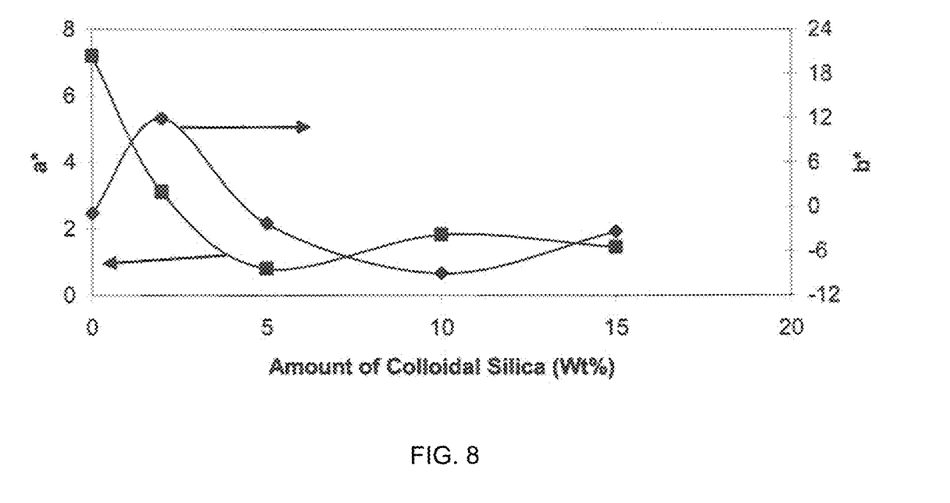
FIG. 8 is a graph of the color components a* and b* as a function of the amount of colloidal silica in the titanium dioxide coatings of the Examples.

FIG. 8 is a graph of the color components a* and b* as a function of the amount of colloidal silica in the titanium dioxide coating. As can be seen in FIG. 8, the value of color components a* and b*, which indicate the way the color is perceived, does not vary greatly with changes in the amount of colloidal silica present in the titanium dioxide coating.

What is claimed is:

1. A method of forming an anatase titanium dioxide coating having a roughened surface on a substrate, comprising:
    preparing a titanium dioxide sol-gel composition;
    adding colloidal silica particles to the titanium dioxide sol-gel composition to form a combined titanium dioxide and colloidal silica sol-gel composition, wherein the colloidal silica particles have an average particle size of about 70 nm to about 100 nm;
    coating the substrate with the combined sol-gel composition; and
    heating the coated substrate at a temperature ranging from about 550° C. to about 650° C. to form a surface roughened anatase titanium dioxide coating;
    wherein the surface roughened titanium dioxide coating has a mean square roughness ranging from about 8 nm to about 12 nm; and
    wherein the combined titanium dioxide and colloidal silica sol-gel composition comprises colloidal silica in an amount less than or equal to about 20 wt % relative to a total weight of the sol-gel composition.

2. The method of claim 1, wherein the combined titanium dioxide and colloidal silica sol-gel composition comprises at least 5 wt % of said colloidal silica particles relative to the total weight of the sol-gel composition.

3. The method of claim 1, wherein the substrate comprises a glass substrate.

4. The method of claim 3, wherein the glass substrate is chosen from clear glass and low-iron glass substrates.

5. A method of improving at least one of antimicrobial properties, self-cleaning properties, hydrophilicity, and activation time of a titanium dioxide coating, comprising:
    preparing a titanium dioxide sol-gel composition;
    adding colloidal silica particles to the titanium dioxide sol-gel composition to form a combined titanium dioxide and colloidal silica sol-gel composition, wherein the colloidal silica particles have an average particle size of about 70 nm to about 100 nm;
    coating a substrate with the combined sol-gel composition; and heating the coated substrate at a temperature ranging from about 550° C. to about 650° C. to form a surface roughened anatase titanium dioxide coating;

wherein the surface roughened titanium dioxide coating has a mean square roughness ranging from about 8 nm to about 12 nm; and wherein the combined titanium dioxide and colloidal silica sol-gel composition comprises colloidal silica in an amount less than or equal to about 20 wt % relative to a total weight of the sol-gel composition.

6. The method of claim 5, wherein the combined titanium dioxide and colloidal silica sol-gel composition comprises at least 5 wt % colloidal silica particles relative to the total weight of the sol-gel composition.

7. The method of claim 5, wherein the substrate is chosen from clear glass and low-iron glass.

8. The method of claim 1, wherein the titanium dioxide sol-gel composition comprises a titanium alkoxide or a titanium chloride.

9. The method of claim 5, wherein the titanium dioxide sol-gel composition comprises a titanium alkoxide or a titanium chloride.

10. The method of claim 1, wherein the combined titanium dioxide and colloidal silica sol-gel composition comprises colloidal silica in an amount less than or equal to about 15 wt % relative to the total weight of the sol-gel composition.

11. The method of claim 5, wherein the combined titanium dioxide and colloidal silica sol-gel composition comprises colloidal silica in an amount less than or equal to about 15 wt % relative to the total weight of the sol-gel composition.

12. The method of claim 1, wherein the combined titanium dioxide and colloidal silica sol-gel composition comprises colloidal silica in an amount of about 5 wt % to about 15 wt % relative to the total weight of the sol-gel composition.

13. The method of claim 5, wherein the combined titanium dioxide and colloidal silica sol-gel composition comprises colloidal silica in an amount of about 5 wt % to about 15 wt % relative to the total weight of the sol-gel composition.

\* \* \* \* \*